(12) United States Patent
Yamamoto et al.

(10) Patent No.: US 7,749,404 B2
(45) Date of Patent: *Jul. 6, 2010

(54) FLUORESCENT DIKETOPYRROLOPYRROLES

(75) Inventors: Hiroshi Yamamoto, Nishinomiya (JP); Norihisa Dan, Yawata (JP); Olof Wallquist, Therwil (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 677 days.

This patent is subject to a terminal disclaimer.

(21) Appl. No.: 11/409,694

(22) Filed: Apr. 24, 2006

(65) Prior Publication Data

US 2006/0186376 A1 Aug. 24, 2006

Related U.S. Application Data

(63) Continuation of application No. 10/481,963, filed as application No. PCT/EP02/06846 on Jun. 20, 2002, now Pat. No. 7,063,806.

(30) Foreign Application Priority Data

Jun. 29, 2001 (EP) .................................. 01810636
Jul. 2, 2001 (EP) .................................. 01810647

(51) Int. Cl.
H05B 33/14 (2006.01)
C09K 11/06 (2006.01)
C08K 5/3415 (2006.01)
C07D 487/04 (2006.01)
C09B 57/00 (2006.01)

(52) U.S. Cl. ............................ 252/301.16; 252/301.31; 428/690; 428/917; 313/503

(58) Field of Classification Search .............. 106/31.15, 106/31.32, 31.64, 498; 428/690, 917; 528/458; 252/301.35, 301.34, 301.22, 301.31, 301.27, 252/301.16; 424/401; 372/53; 420/7
See application file for complete search history.

(56) References Cited

U.S. PATENT DOCUMENTS

| 4,585,878 | A | 4/1986 | Jost et al. ..................... 548/453 |
| 5,298,063 | A | 3/1994 | Mizuguchi et al. ............ 106/21 |
| 5,973,146 | A | 10/1999 | Rochat et al. ................. 544/144 |
| 6,603,020 | B1 * | 8/2003 | Moretti et al. ................. 548/453 |
| 7,001,677 | B2 * | 2/2006 | Otani et al. ................... 428/690 |
| 7,063,806 | B2 * | 6/2006 | Yamamoto et al. ........ 252/301.16 |
| 2004/0171847 | A1 | 9/2004 | Morton et al. ................ 548/453 |

FOREIGN PATENT DOCUMENTS

| DE | 3713459 | 8/1988 |
| EP | 0499011 | 8/1992 |
| EP | 0563009 | 9/1993 |
| EP | 0811625 | 12/1997 |
| EP | 1087005 | * 3/2001 |
| EP | 1087006 | * 3/2001 |
| WO | 96/08537 | 3/1996 |
| WO | 98/25927 | 6/1998 |
| WO | 98/32802 | 7/1998 |

OTHER PUBLICATIONS

Derwent Abstr. 2002-319245 [36] for JP 2001297881 (2001).
Derwent Abstr. 2002-210369 [27] for JP 2001257078 (2001).
Derwent Abstr. 2002-210368 [27] for JP 2001257077 (2001).
Patent Abstracts of Japan Publication No. 02296891 (1990).
Patent Abstracts of Japan Publication No. 05320633 (1993).
Patent Abstracts of Japan Publication No. 09003448 (1997).
English Language Abstract of DE 3713459 (1988).

* cited by examiner

Primary Examiner—C. Melissa Koslow
(74) Attorney, Agent, or Firm—Shiela A. Loggins

(57) ABSTRACT

The present invention relates to fluorescent diketopyrrolopyrroles ("DPPs") of the formula

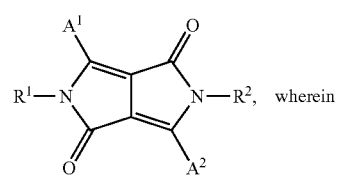

(I)

$A^1$ and $A^2$ independently from each other stand for

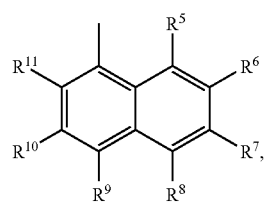

(II)

characterized in that that at least two adjacent substituents $R^5$ to $R^{11}$ form an aromatic or aliphatic fused ring system, or at least one substituent $R^5$ to $R^{11}$ is cycloalkyl, aralkyl, alkenyl, cycloalkenyl, alkynyl, a hydroxyl group, a mercapto group, alkylthio, an aryl thioether group, a heterocyclic group, halogen, haloalkyl, haloalkenyl, haloalkynyl, a cyano group, an aldehyde group, a carbonyl group, a carboxyl group, an ester group, a carbamoyl group, a nitro group, a silyl group, a siloxanyl group, a substituted or unsubstituted vinyl, arylamino or diarylamino group; a process for their preparation and their use for the preparation of inks, colorants, pigmented plastics for coatings, non-impact-printing material, color filters, cosmetics, or for the preparation of polymeric ink particles, toners, dye lasers and electroluminescent devices.

The fluorescent diketopyrrolopyrroles ("DPPs") of the formula I exhibit a high lightfastness, a high heat stability, especially in plastics. A luminescent device comprising a DPP compound of formula I is high in the efficiency of electrical energy utilisation, high in luminance and high in colour purity.

2 Claims, No Drawings

FLUORESCENT DIKETOPYRROLOPYRROLES

This is a continuation of U.S. application Ser. No. 10/481,963 filed Dec. 22, 2003, now U.S. Pat. No. 7,063,806 which is a 371 of PCT/EP02/06846, filed Jun. 20, 2002, the disclosures of which are incorporated herein in its entirety by reference.

The present invention relates to fluorescent diketopyrrolopyrroles ("DPPs") of the formula I, a process for their preparation and their use for the preparation of inks, colorants, pigmented plastics for coatings, non-impact-printing material, color filters, cosmetics, or for the preparation of polymeric ink particles, toners, dye lasers and electroluminescent devices. The fluorescent diketopyrrolopyrroles ("DPPs") of the formula I exhibit high lightfastness as well as high heat stability, especially in plastics. A luminescent device comprising a DPP compound of formula I is high in the efficiency of electrical energy utilisation, high in luminance and high in colour purity.

U.S. Pat. No. 4,579,949 describes a process for the preparation of DPPs which are unsubstituted at the nitrogen atoms of the pyrrolo-rings. Especially example 45 describes a DPP-compound of the formula

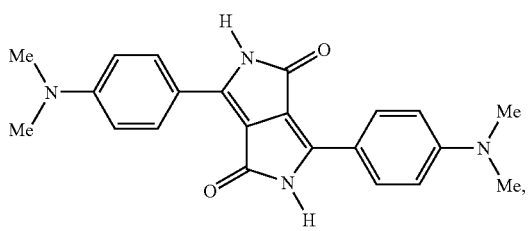

which is violet, exhibits only insufficient fluorescence and solubility.

EP-A-133,156 claims generically DPP-compounds. However, compounds of formula I are not mentioned explicitly and no teaching is given that DPP-compounds of formula I could exhibit a red or orange fluorescence.

EP-A 499,011 describes electroluminescent devices comprising DPP-compounds. Particularly, in example 1 the DPP-derivative of formula

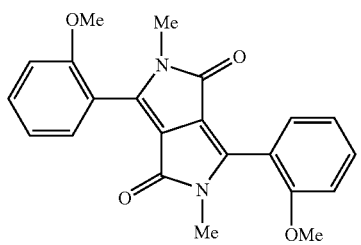

is disclosed. However, no teaching is given with regard to the fluorescence of DPP-compounds and a way to obtain DPP-compounds exhibiting a red or orange fluorescence.

WO 98/33862 describes the use of the DPP-compound of formula

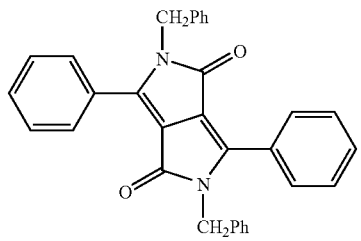

as a guest molecule in electroluminescent devices. However, no teaching is given with regard to the fluorescence of DPP-compounds and a way to obtain DPP-compounds exhibiting a red or orange fluorescence.

EP-A-1087005 relates to fluorescent diketopyrrolopyrroles ("DPPs") of the formula I'

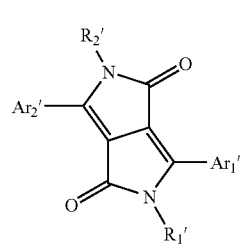

wherein $R_1$ and $R_2$, independently from each other, stand for $C_1$-$C_{25}$-alkyl, allyl which can be substituted one to three times with $C_1$-$C_3$alkyl or $Ar_3'$, $-CR_3'R_4'-(CH_2)_m-Ar_3$, wherein $R_3'$ and $R_4'$ independently from each other stand for hydrogen or $C_1$-$C_4$alkyl, or phenyl which can be substituted on to three times with $C_1$-$C_3$ alkyl, $Ar_3'$ stands for phenyl or 1- or 2-naphthyl which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4, and wherein $C_1$-$C_{25}$-alkyl or $-CR_3'R_4'-(CH_2)_m-Ar_3'$, preferably $C_1$-$C_{25}$-alkyl, can be substituted with a functional group capable of increasing the solubility in water such as a tertiary amino group, $-SO_3^-$, or $PO_4^{2-}$, $Ar_1'$ and $Ar_2'$, independently from each other, stand for

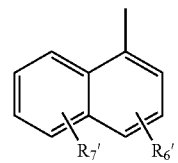

wherein $R_6'$ and $R_7'$, independently from each other, stand for hydrogen, $C_1$-$C_8$alkyl, $-NR_8R_9$, $-OR_{10}$, $-S(O)_nR_8$, $-Se(O)_nR_8$, or phenyl, which can be substituted one to three times with $C_1$-$C_8$alkyl or $C_1$-$C_8$alkoxy, but do not stand simultaneously for hydrogen, wherein $R_8'$ and $R_9'$, independently from each other, stand for hydrogen, $C_1$-$C_{25}$-alkyl, $C_5$-$C_{12}$-cycloalkyl, $-CR_3R_4-(CH_2)_m-Ph$, $R_{10}'$, wherein $R_{10}'$ stands for $C_8$-$C_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, wherein Ph, the aryl and heterocyclic radical can be substituted one to three times with $C_1$-$C_8$alkyl, $C_1$-$C_8$alkoxy, or halogen, or $R_8'$ and $R_9'$ stand for —C(O)$R_{10}'$, wherein $R_{11}'$ can be $C_1$-$C_{25}$-alkyl, $C_5$-$C_{12}$-cycloalkyl, $R_{10}'$, —O$R_{12}'$ or —N$R_{13}'R_{14}'$, wherein $R_{12}'$, $R_{13}'$, and $R_{14}'$ stand for $C_1$-$C_{25}$-alkyl, $C_5$-$C_{12}$-cycloalkyl, $C_8$-$C_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, wherein the aryl and heterocyclic radical can be substituted one to three times with $C_1$-$C_8$alkyl or $C_1$-$C_8$alkoxy, or —N$R_8'R_9'$ stands for a five- or six-membered heterocyclic radical in which $R_8'$ and $R_9'$ together stand for tetramethylene, pentamethylene, —CH$_2$—CH$_2$—O—CH$_2$—CH$_2$—, or —CH$_2$—CH$_2$—N$R_5$—CH$_2$—CH$_2$—, preferably —CH$_2$—CH$_2$—CH$_2$—CH$_2$—, and n stands for 0, 1, 2 or 3. The DPP compounds can be used for the preparation of inks, colorants, pigmented plastics for coatings, non-impact-printing material, color filters, cosmetics, or for the preparation of polymeric ink particles, toners, dye lasers and electroluminescent devices. EP-A-1087006 describes electroluminescent devices comprising the DPP compounds of formula (I').

Hence, the object of this invention was to provide red or orange fluorescent compounds with a high heat stability, a good solubility in polymers, hydrocarbon based fuels, lubricants, and water, a high light stability, and the ability to be used in plastics, especially polyamides, without decomposition and loss of lightfastness, and in paints and with a high electroluminescent (EL) emission intensity.

Surprisingly, it was found that the above object was solved by a diketopyrrolopyrrole of the formula I

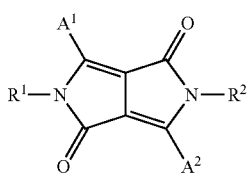

wherein $R^1$ and $R^2$ may be the same or different and are selected from a $C_1$-$C_{25}$alkyl group, an allyl group, which can be substituted one to three times with $C_1$-$C_3$alkyl, a cycloalkyl group, an alkenyl group, a cycloalkenyl group, an alkynyl group, a heterocyclic group, halogen, haloalkyl, haloalkenyl, haloalkynyl, a ketone or aldehyde group, a carboxyl group, an ester group, a carbamoyl group, a silyl group, a siloxanyl group, $A^3$ or —C$R^3R^4$—(CH$_2$)$_m$-$A^3$ wherein $R^3$ and $R^4$ independently from each other stand for hydrogen or $C_1$-$C_4$alkyl, or phenyl which can be substituted one to three times with $C_1$-$C_3$alkyl, $A^3$ stands for cycloalkyl, heterocyclic group, preferably aryl, in particular phenyl or 1- or 2-naphthyl which can be substituted one to three times with $C_1$-$C_8$alkyl and/or $C_1$-$C_8$alkoxy, and m stands for 0, 1, 2, 3 or 4, wherein $C_1$-$C_{25}$alkyl or —C$R^3R^4$—(CH$_2$)$_m$-$A^3$, preferably $C_1$-$C_{25}$alkyl, can be substituted with a functional group capable of increasing the solubility in water, such as a tertiary amino group, —SO$_3^-$ or —PO$_4^{2-}$, $A^1$ and $A^2$ independently from each other stand for

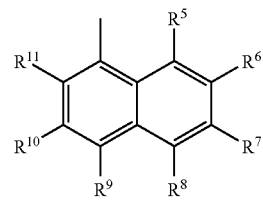

wherein $R^5$ to $R^{11}$ may be the same or different and are selected from hydrogen, $C_1$-$C_{25}$alkyl group, cycloalkyl, aralkyl, alkenyl, cycloalkenyl, alkynyl, a hydroxyl group, a mercapto group, alkoxy, alkylthio, an aryl ether group, an aryl thioether group, aryl, a heterocyclic group, halogen, haloalkyl, haloalkenyl, haloalkynyl, a cyano group, an aldehyde group, a carbonyl group, a carboxyl group, an ester group, a carbamoyl group, an amino group, an alkylamino group, a di(alkyl)amino group, a nitro group, a silyl group, a siloxanyl group, a substituted or unsubstituted vinyl group, a substituted or unsubstituted arylamino group and a substituted or unsubstituted diarylamino group, or at least two adjacent substituents $R^5$ to $R^{11}$ form an aromatic or aliphatic fused ring system, with the proviso at least two adjacent substituents $R^5$ to $R^{11}$ form an aromatic or aliphatic fused ring system, or at least one substituent $R^5$ to $R^{11}$ is cycloalkyl, aralkyl, alkenyl, cycloalkenyl, alkynyl, a hydroxyl group, a mercapto group, alkylthio, an aryl thioether group, a heterocyclic group, halogen, haloalkyl, haloalkenyl, haloalkynyl, a cyano group, an aldehyde group, a carbonyl group, a carboxyl group, an ester group, a carbamoyl group, an amino group, a nitro group, a silyl group, a siloxanyl group, a substituted or unsubstituted vinyl, arylamino or diarylamino group.

Preferably, at least two adjacent substituents $R^5$ to $R^{11}$ form an aromatic or aliphatic fused ring system, or at least one substituent $R^5$ to $R^{11}$ is a substituted or unsubstituted vinyl group or a substituted or unsubstituted diarylamino group.

The wording "at least two adjacent substituents $R^5$ to $R^{11}$ form an aromatic or aliphatic fused ring system" means two adjacent substituents $R^5$ to $R^{11}$ can form an aromatic ring, such as a phenyl or naphthyl ring, an aliphatic ring, such as a cyclohexyl ring, or a heterocyclic ring, such as a pyridine or pyrrole ring, wherein two or more of such rings can form a fused ring system with the naphthyl group to which they are bonded, such as a benzophenanthryl, pyrenyl, benzo[a]pyrenyl or benzo[a]anthranyl group.

If the naphthyl substituent is substituted by a diarylamino group, $A^1$ and $A^2$ independently from each other can stand for

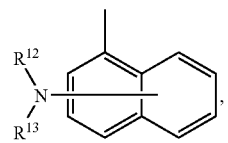

wherein $R^{12}$ and $R^{13}$ are independently of each other $C_8$-$C_{24}$aryl, such as phenyl, 1-naphthyl, 2-naphthyl, 4-biphenyl, phenanthryl, terphenyl, pyrenyl, 2- or 9-fluorenyl or anthracenyl, preferably $C_8$-$C_{12}$aryl such as phenyl, 1-naphthyl, 2-naphthyl, 4-biphenyl, which may be unsubstituted or substituted by, for example, $C_1$-$C_8$alkyl, $C_1$-$C_8$alkoxy or a group —NR$^{12a}$NR$^{13a}$, wherein R$^{12a}$ and R$^{13a}$ are independently of each other C$_8$-C$_{12}$aryl such as phenyl, 1-naphthyl, 2-naphthyl, 4-biphenyl, which may be unsubstituted or substituted by, for example, C$_1$-C$_8$alkyl or C$_1$-C$_8$alkoxy, or R$^{12}$ and R$^{13}$ or R$^{12a}$ and R$^{13a}$ form together with the nitrogen atom to which they are bonded a five or six membered heterocyclic ring, such as

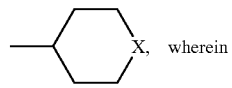, wherein

X is O, S or NR$^{40}$, wherein R$^{40}$ is hydrogen or C$_1$-C$_8$alkyl.

If the naphthyl substituent is substituted by a vinyl group, A$^1$ and A$^2$ independently from each other can stand for

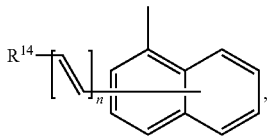

wherein n is an integer of 1 to 4 and R$^{14}$ is C$_8$-C$_{24}$aryl, such as phenyl, 1-naphthyl, 2-naphthyl, 4-biphenyl, phenanthryl, terphenyl, pyrenyl, 2- or 9-fluorenyl or anthracenyl, preferably C$_8$-C$_{12}$aryl such as phenyl, 1-naphthyl, 2-naphthyl, 4-biphenyl, which may be unsubstituted or substituted.

The groups of the following formula are examples of A$^1$ and A$^2$, wherein R$^9$ and R$^{10}$ form a heterocyclic ring, which is part of a fused ring system:

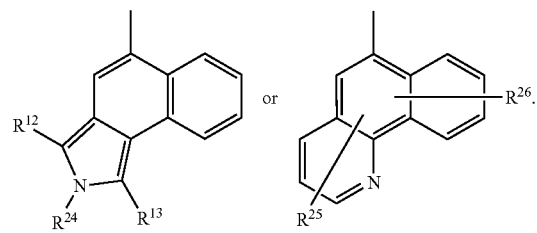

wherein R$^{12}$ and R$^{13}$ have the meanings given above, R$^{24}$ is a C$_1$-C$_6$alkyl group and R$^{25}$ and R$^{26}$ are independently of each other hydrogen, C$_1$-C$_8$alkyl, C$_1$-C$_8$alkoxy or C$_1$-C$_8$alkylthio. Further examples of A$^1$ and A$^2$, wherein two adjacent substituents R$^5$ to R$^{11}$ form an aromatic fused ring system are given below.

A$^1$ and A$^2$ independently of each other preferably stand for

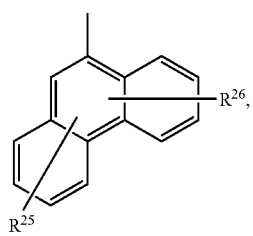

-continued

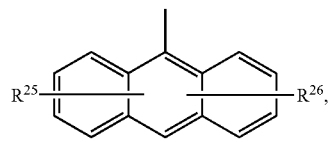

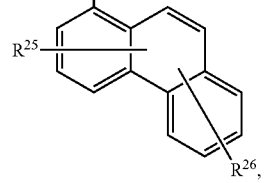

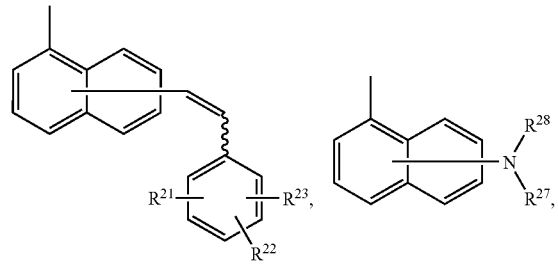

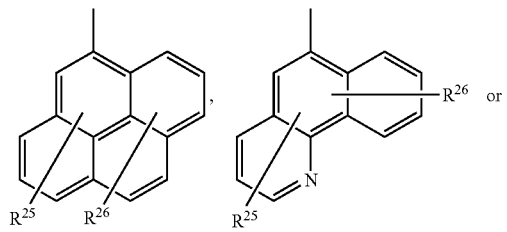

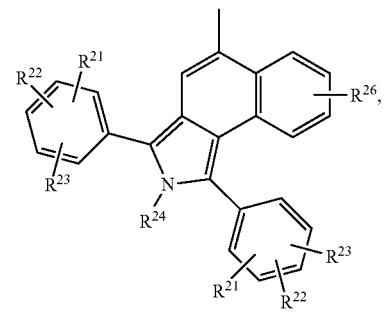

wherein R$^{21}$, R$^{22}$, R$^{23}$, R$^{25}$ and R$^{26}$ are independently of each other hydrogen, C$_1$-C$_8$alkyl, a hydroxyl group, a mercapto group, C$_1$-C$_8$alkoxy, C$_1$-C$_8$alkylthio, halogen, halo-C$_1$-C$_8$alkyl, a cyano group, an aldehyde group, a ketone group, a carboxyl group, an ester group, a carbamoyl group, an amino group, a nitro group, a silyl group or a siloxanyl group, R$^{24}$ is a C$_1$-C$_8$alkyl group and R$^{27}$ and R$^{28}$ are independently of each other

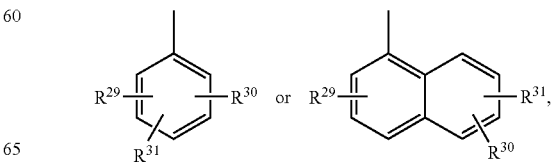

wherein $R^{29}$, $R^{30}$ and $R^{31}$ are independently of each other hydrogen, $C_1$-$C_8$alkyl, $C_1$-$C_8$alkoxy or a group —$NR^{32}R^{33}$, wherein $R^{32}$ and $R^{33}$ are independently of each other

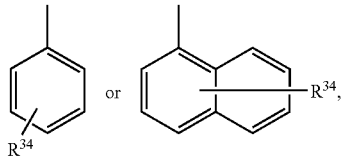

wherein $R^{34}$ is hydrogen, $C_1$-$C_8$alkyl or $C_1$-$C_8$alkoxy. Preferably $R^{21}$, $R^{22}$, $R^{23}$, $R^{25}$ and $R^{26}$ are independently of each other hydrogen, $C_1$-$C_8$alkyl, $C_1$-$C_8$alkoxy or $C_1$-$C_8$alkylthio.

More preferred $A^1$ and $A^2$ independently of each other stand for

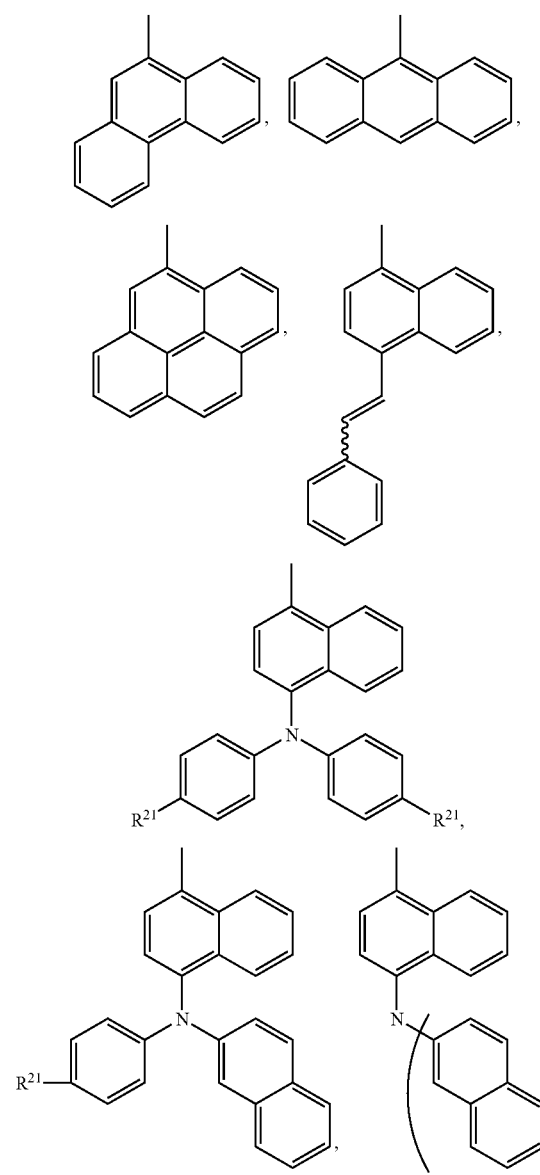

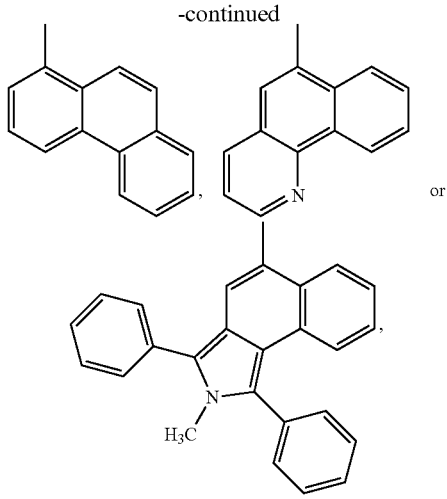

wherein $R^{21}$ is hydrogen, $C_1$-$C_8$alkyl or $C_1$-$C_8$alkoxy.

$R^1$ and $R^2$ may be the same or different. Preferably, $R^1$ and $R^2$ are the same and are selected from allyl, $C_1$-$C_8$alkyl, such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, cycloalkyl, in particular a cyclohexyl group, which can be substituted one to three times with $C_1$-$C_8$alkyl and/or $C_1$-$C_8$alkoxy, in particular cyclohexyl or 2,6-di-iso-propylcyclohexyl, silyl, in particular tri($C_1$-$C_8$alkyl)silyl, such as a trimethylsilyl group, phenyl, biphenyl or 1- or 2-naphthyl which can be substituted one to three times with $C_1$-$C_8$alkyl and/or $C_1$-$C_8$alkoxy, or —$CR^3R^4$—$(CH_2)_m$-$A^3$ wherein $R^3$ and $R^4$ stand for hydrogen, $A^3$ stands phenyl, biphenyl or 1- or 2-naphthyl which can be substituted one to three times with $C_1$-$C_8$alkyl and/or $C_1$-$C_8$alkoxy, such as $C_1$-$C_8$alkylphenyl, di($C_1$-$C_8$alkyl)phenyl, in particular 3-methylphenyl, 4-methylphenyl, 3,5-dimethylphenyl, 3,5-di-tert.-butylphenyl and 2,5- and 2,6-diisopropylphenyl, and m stands for 0 or 1.

Examples of preferred compounds are listed below:

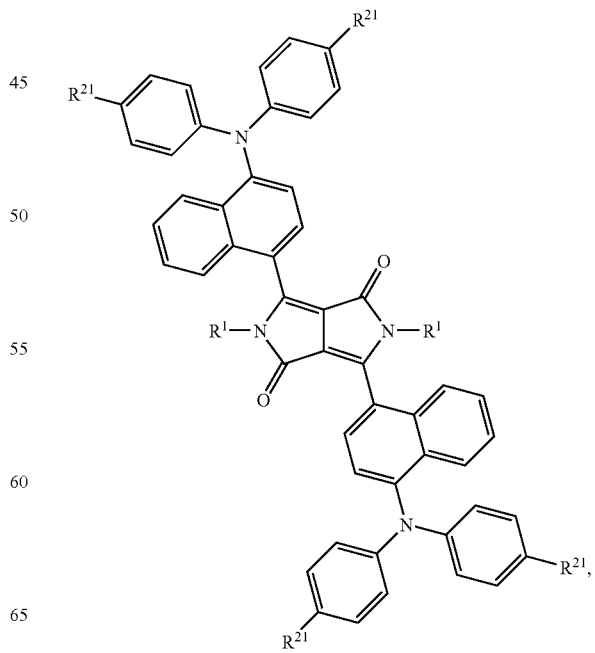

-continued

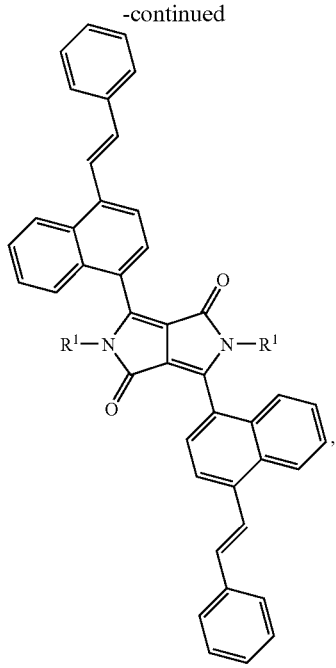

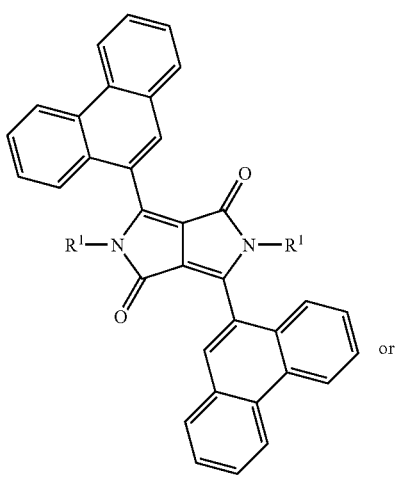

or

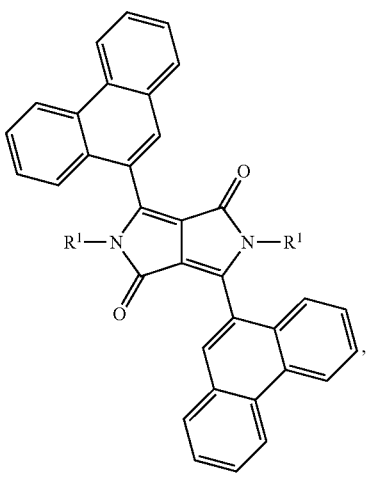

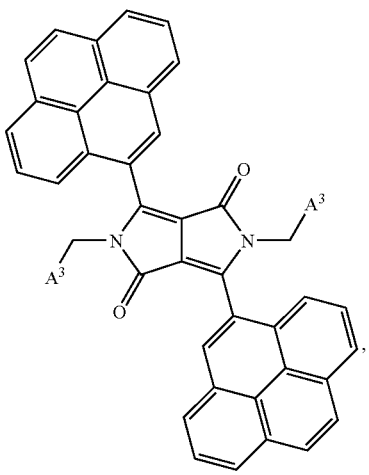

wherein $R^1$ is allyl, $C_1$-$C_8$alkyl, such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, tri($C_1$-$C_8$alkyl)silyl, such as trimethylsilyl, —$CH_2$-$A^3$, —$CHCH_3$-$A^3$ or —$CH_2$—$CH_2$-$A^3$, wherein $A^3$ stands for phenyl, which can be substituted one or two times with $C_1$-$C_8$alkyl, such as 3-methylphenyl, 3,5-dimethylphenyl, 3,5-di-tert.-butylphenyl and 2,5- and 2,6-diisopropylphenyl, and $R^{21}$ is hydrogen, $C_1$-$C_4$alkyl or $C_1$-$C_4$alkoxy, wherein the following compounds of the formula I are particularly preferred:

wherein $R^1$ is allyl, benzyl, 3-methylbenzyl, 4-methylbenzyl, 3,5-dimethylbenzyl, 3,5di-tert.-butylbenzyl, trimethylsilyl, in particular methyl, ethyl, n-propyl, isopropyl, n-butyl, isobutyl or tert.-butyl;

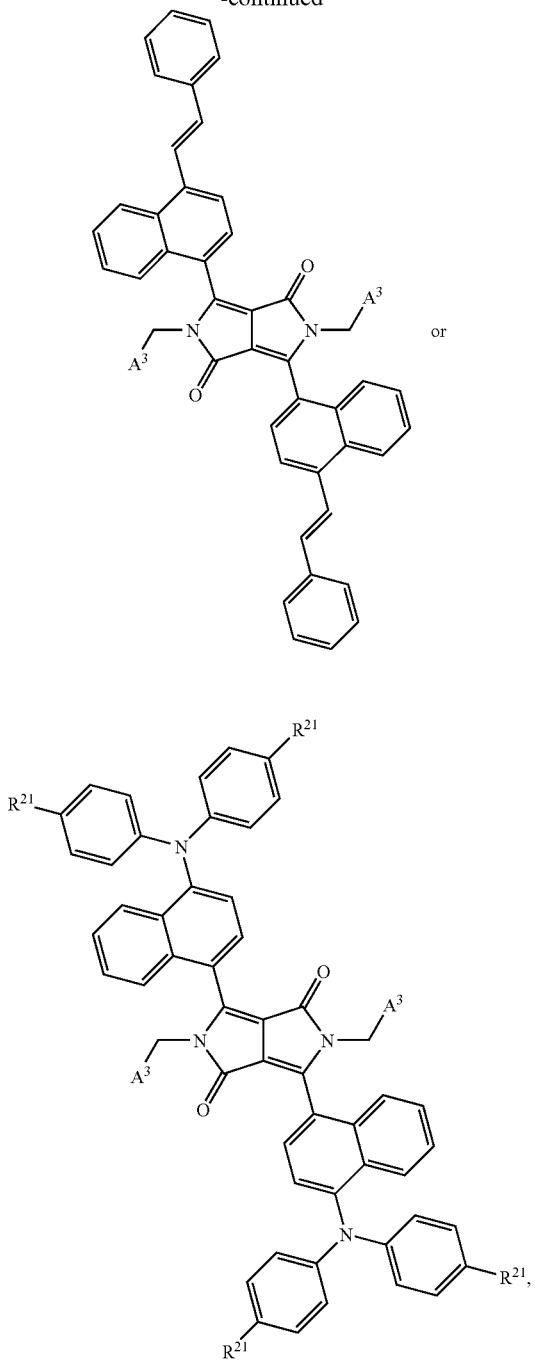

wherein $A^3$ is phenyl, 3-methylphenyl, 4-methylphenyl, 3,5-dimethylphenyl, 3,5-di-tert.-butylphenyl and $R^{21}$ is hydrogen, $C_1$-$C_4$alkyl or $C_1$-$C_4$alkoxy.

The inventive DPP-compounds I can be synthesized according to or in analogy to methods well known in the art, such as described in EP-A-133,156, WO90/01480, EP-A-1087005 and EP-A-1087006.

Accordingly, the present invention also relates to a process for the preparation of the DPP compounds of formula I by treating in a first step the DPP derivative of formula (II)

with a base, then, in a second step, treating the reaction mixture obtained in the first step with a usual alkylating agent or two usual alkylating agents, wherein in the first step the base is a hydride, such as sodium hydride, lithium hydride, or potassium hydride, an alkali metal alkoxide, such as sodium or potassium tert.-butoxide, sodium tert.-amylate, or a carbonate, such as sodium or potassium carbonate and the alkylating agent is a sulfonate, such as a tosylate or mesylate, carbonate, sulfate, or halogen compound of the formula $(R^1)_{1\ or\ 2}X$ and/or $(R^2)_{1\ or\ 2}X$, wherein X stands for $RSO_3^-$, wherein R is alkyl or aryl, such as $CH_3SO_2O$—, (p-$CH_3$-phenyl)$SO_2O$— or (2,4,6-trimethyl-phenyl)$SO_2O$—, —OC(O)O—, —$OSO_2O$—, or halogen such as chlorine, bromine or iodine, preferably chlorine, bromine or iodine, particularly preferred $R^1X$ and $R^2X$, wherein X is bromine or iodine (for details see EP-A-1,087,005).

The DPP compounds of formula II are described e.g. in U.S. Pat. No. 4,579,949, and/or can be prepared according to the method described therein (or in U.S. Pat. No. 4,659,775), in which an appropriate nitrile is reacted with a corresponding dialkyl or diaryl succinate, e.g. NC—$Ar^1$ and NC—$Ar^2$ are reacted with sodium tert.-amyl alcohol followed by the addition of diisopropyl succinate.

Water-soluble compounds I, i.e. inventive compounds I being substituted with a functional group capable of increasing the solubility in water such as a tertiary amino group, $SO_3^-$, or $PO_4^{2-}$, can be prepared by using well-known methods in the art. The following routes are representative examples, and, hence, do not restrict the invention just to these examples:

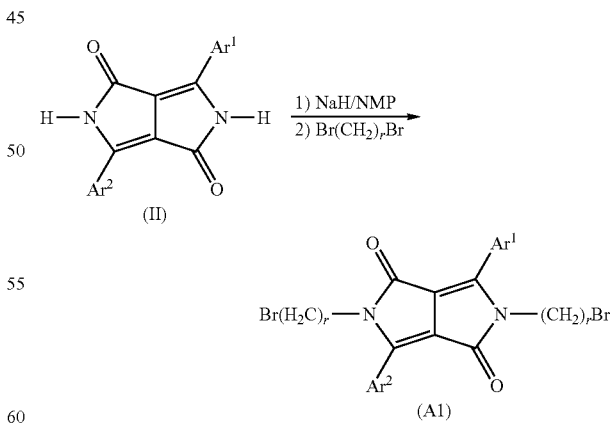

wherein r stands for an integer from usually 2 to 25; instead of linear alkyl groups, one could also use branched alkyl groups or aralkyl groups such as Br—$(CH_2)_{r-1}$-aryl-$(CH_2)_{2r}$—Br, $r_1$ and $r_2$ usually being whole numbers in the range of from 0 to 10;

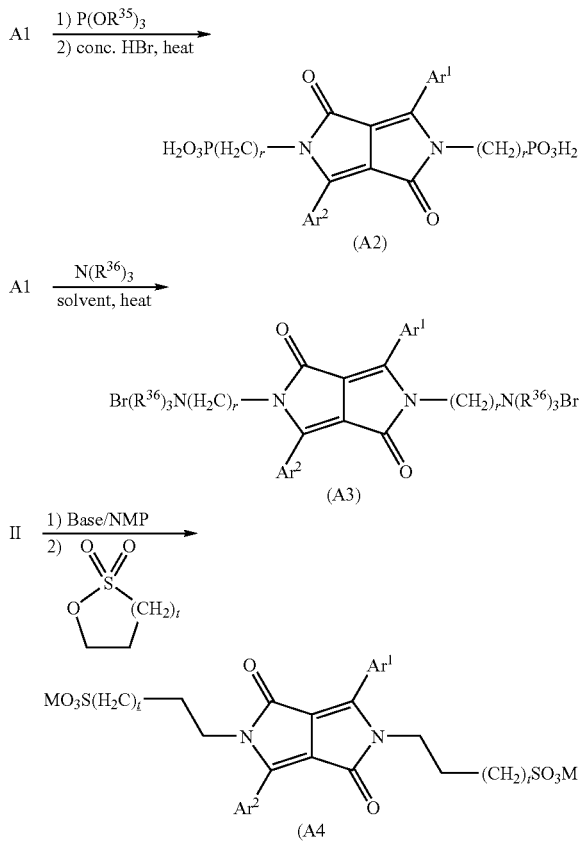

wherein $R^{35}$ and $R_{36}$ are a hydrogen atom, a $C_1$-$C_{25}$alkyl group, a cycloalkyl group, an aryl group or an aralkyl group, M stands for a metal ion such as sodium or potassium, and t is 1 or 2.

Compounds I are also available in analogy to the method described in EP-A-353,184, which comprises reacting a DPP compound of formula III

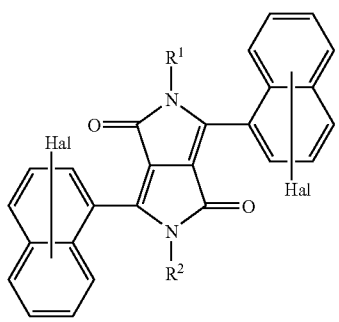

wherein Hal stands for halogen such as fluorine, chlorine, bromine or iodine, preferably chlorine or bromine, with a nucleophilic agent such as a secondary amine, $HNR^{12}R^{13}$, preferably in a molar ratio of DPP III:nucleophilic agent in the range of 1.2:1 to 0.8:1, or, if $R^2$ has the same meaning as $R^1$ in the range of from 1:2.5 to 1:1, in the presence of an anhydrous dipolar aprotic solvent, and of an anhydrous base in an amount in the range of from usually 0.1 to 15 moles per mole of the nucleophilic agent, at a temperature in the range of from usually 100 to 220° C. and under a pressure generally in the range of from 100 to 300 kPa (for details see EP-A-1, 087,005).

The DPP compounds of formula III are known and/or can be prepared e.g. according to the method described in U.S. Pat. No. 4,579,949.

The term "halogen" means fluorine, chlorine, bromine and iodine.

The term "alkyl" is typically linear or branched $C_1$-$C_{25}$alkyl, such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl, octadecyl, eicosyl, heneicosyl, docosyl, tetracosyl or pentacosyl, preferably $C_1$-$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl, more preferably $C_1$-$C_4$alkyl such as typically methyl, ethyl, n-propyl, isopropyl, n-butyl, sec.-butyl, isobutyl or tert.-butyl.

The term "alkenyl group" means an unsaturated aliphatic hydrocarbon group having typically 2 to 8 carbon atoms and containing one or more double bonds, such as vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl or 1,4-pentadien-3-yl. The term "alkynyl group" means an unsaturated aliphatic hydrocarbon group having-typically 2 to 8 carbon atoms and containing a triple bond, such as ethynyl, 1-propyn-3-yl, 1-butyn4-yl, 1-pentyn-5-yl, 2-methyl-3-butyn-2-yl, 1,4pentadiyn-3-yl, 1,3-pentadiyn-5-yl, 1-hexyn-yl, cis-3-methyl-2-penten-4-yn-1-yl, trans-3-methyl-2-penten-4-yn-1-yl, 1,3-hexadiyn-5-yl or 1-octyn8-yl.

The terms "haloalkyl, haloalkenyl and haloalkynyl" mean groups given by partially or wholly substituting the above-mentioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{42}R^{43}R^{44}$, wherein $R^{42}$, $R^{43}$ and $R^{44}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group. The term "siloxanyl group" means a group of formula —O—$SiR^{42}R^{43}R^{44}$, wherein $R^{42}$, $R^{43}$ and $R^{44}$ are as defined above, such as a trimethylsiloxanyl group.

The term "alkoxy group" is typically $C_1$-$C_8$alkoxy, such as methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of ether linkage is replaced by a sulfur atom. The term "aryl ether group" means an aromatic hydrocarbon group linking through intermediation of an ether linkage, such as phenoxy and the like, in which the aromatic hydrocarbon group may be unsubstituted or substituted. The term "aryl thioether group" means the same groups as the aryl ether groups, except that the oxygen atom of the ether linkage is replaced by a sulfur atom.

The term "aryl group" is typically $C_8$-$C_{24}$aryl, such as 1-naphthyl, 2-naphthyl, 4-biphenyl, phenanthryl, terphenyl, pyrenyl, 2- or 9-fluorenyl or anthracenyl, preferably $C_8$-$C_{12}$aryl such as phenyl, 1-naphthyl, 2-naphthyl, 4-biphenyl, which may be unsubstituted or substituted.

The term "aralkyl group" is typically $C_7$-$C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ωω-dimethyl-ω-phenyl-butyl, in which both the aliphatic hydrocarbon group and aromatic hydrocarbon group may be unsubstituted or substituted.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted.

The term "heterocyclic group" is a ring with five to seven ring atoms, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the abovementioned mono- or bicyclic heterocyclic radicals.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

The "aromatic ring or aliphatic ring formed by $R^5$ to $R^{11}$ in conjunction with an adjacent substituent" may be unsubstituted or substituted, can contain 1 to 3, preferably 1 heteroatom, which is selected from nitrogen, oxygen and sulfur, and is preferably a five or six membered ring, such as a phenyl, pyridinyl or pyrrolyl group, which can be further substituted. Examples of further five or six membered rings are given in the definition of "aryl group", "cycloalkyl group" and "heterocyclic group".

In addition, the present invention relates further to an electroluminescent device having the fluorescent compound of formula I between an anode and a cathode and emitting light by the action of electrical energy.

Thin film type electroluminescent devices usually consist essentially of a pair of electrodes and at least one charge transporting layer in between. It is presently common to prepare organic electroluminescent ("EL") devices which contain an organic fluorescent substance by a vacuum evaporation process, e.g. described in Appl. Phys. Lett., 51, 913 (1987). In general, two types of such vacuum evaporation processes are applied according to the constitution of light emitting material: a one-component type process and a two-components type process (or "Host-Guest type" or "binary system") process (e.g. described in J. Appl. Phys., 65, 3610 (1989)).

For emitting a light of red, green or blue color in a one-component system, the light emitting materials themselves have to emit an intense fluorescence of red, green or blue color. Further, a vacuum evaporation process has to give a deposited film of uniform quality, and the film thus formed has to be endowed with appropriate ("carrier") mobility for positive holes and/or electrons i.e. properties of a semiconductor.

JP-A2 2,296,891 (Ricoh) claims an electroluminescent element comprising a positive electrode, a negative electrode and one organic compound layer or a plurality of organic compound layers held between the positive and negative electrodes, but no hole transporting substance. At least one layer of said organic compound layers is a layer containing a pyrrolopyrrole compound represented by the following formula II″

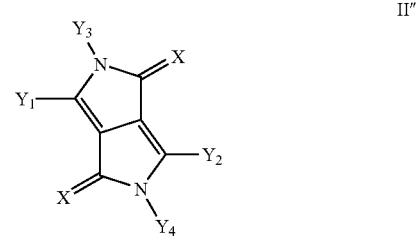

wherein $Y_1$ and $Y_2$ independently from each other represent a substituted or unsubstituted alkyl, cycloalkyl or aryl group, $Y_3$ and $Y_4$ independently represent a hydrogen atom or a substituted or unsubstituted alkyl or aryl group, and X represents an oxygen or a sulfur atom. Only four compounds are mentioned explicitly, namely wherein X stands for oxygen in all cases, and wherein (a) $Y_3=Y_4$=methyl and $Y_1=Y_2$=p-tolyl, (b) $Y_3=Y_4$=methyl and $Y_1=Y_2$=hydrogen, (c) $Y_3=Y_4$=hydrogen and $Y_1=Y_2$=p-tolyl, and (d) $Y_3=Y_4=Y_1$=hydrogen and $Y_2$=p-chlorophenyl.

JP-A2 5,320,633 (Sumitomo) claims an organic EL device having a light emitting layer comprising a light emitting material in an amount of 0.005 to 15 parts by weight of a DPP compound between a pair of electrodes, wherein at least one electrode being transparent or semi-transparent.

JP-A2 9003448 (Toyo Ink) claims an organic EL element having between a pair of electrodes a luminous layer containing a DPP-compound as electron-transporting material or an organic compound thin film layer including a luminous layer and an electron-injecting layer wherein the electron-injecting layer contains a DPP compound as the electron-transporting material. In addition, another EL element further comprising a hole-injecting layer is claimed.

EP-A 499,011 claims an organic EL element comprising a DPP compound. Only systems having no electron-transporting layers are verified. Further, only highly crystalline organic pigments should be employed for a light emitting material. However, one of the requirements for light emitting materials is its morphological stability. Crystalline materials show a tendency to be morphologically modulated in the evaporated film. This becomes a disadvantage for ensuring device durability.

EP-A-1,087,006 relates to an electroluminescent device comprising in this order (a) an anode, (b) a hole transporting layer, (c) a light-emitting layer, (d) optionally an electron transporting layer and (e) a cathode and a light-emitting substance, wherein the light-emitting substance is a diketopyrrolopyrrole ("DPP") represented by formula I'.

Hence, a further object of this invention was to provide electroluminescent devices emitting yellow, orange or red light, wherein organic light-emitting materials should be used fulfilling intense photoluminescence in the solid state for the one-component system, and/or the Host in the binary system, and in the solution state for the Guest in the binary system, carrier mobility for a positive hole and/or an electron, necessary properties for vacuum evaporation and deposition (such as ability to sublime or evaporate), the ability for a homogeneous film formation, the property of exhibiting a "pure" color, the ability that the electronic potential should match with the electrodes and/or with the substances adjacent to, compatibility of the solid host and the molecular guest in case binary systems are desired, high durability (thermal, electrical etc.) and morphological stability.

This object was solved by an electroluminescent device, comprising a fluorescent compound of formula I.

Typical constitutions of latest organic electroluminescent devices are:

(i) an anode/a hole transporting layer/an electron transporting layer/a cathode, in which the compounds of the formula I are used either as positive-hole transport compound, which is exploited to form the light emitting and hole transporting layers, or as electron transport compound, which can be exploited to form the light-emitting and electron transporting layers (an anode/a hole transporting layer/a light-emitting layer/a cathode), and (ii) an anode/a hole transporting layer/a light-emitting layer/an electron transporting layer/a cathode, in which the compounds of the formula I form the light-emitting layer regardless of whether they exhibit positive-hole or electron transport properties in this constitution, and (iii) an anode/a hole injection layer/a hole transporting layer/a light-emitting layer/an electron transporting layer/a cathode, and (iv) an anode/a hole transporting layer/a light-emitting layer/a positive hole inhibiting layer/an electron transporting layer/a cathode, and (v) an anode/a hole injection layer/a hole transporting layer/a light-emitting layer/a positive hole inhibiting layer/an electron transporting layer/a cathode.

Thin film type electroluminescent devices usually consist essentially of a pair of electrodes and at least one charge transporting layer in between. Usually two charge transporting layers, a hole transporting layer (next to the anode) and an electron transporting layer (next to the cathode) are present. Either one of them contains—depending on its properties as hole-transporting or electron-transporting material—an inorganic or organic fluorescence substance as light-emitting material. It is also common, that a light-emitting material is used as an additional layer between the hole-transporting and the electron-transporting layer. In the above mentioned device structure, a hole injection layer can be constructed between a anode and a hole transporting layer and/or a positive hole inhibiting layer can be constructed between a light emitting layer and a electron transporting layer to maximise hole and electron population in the light emitting layer, reaching large efficiency in charge recombination and intensive light emission.

The devices can be prepared in several ways. Usually, vacuum evaporation is used for the preparation. Preferably, the organic layers are laminated in the above order on a commercially available indium-tin-oxide ("ITO") glass substrate held at room temperature, which works as the anode in the above constitutions. The membrane thickness is preferably in the range of 1 to 10,000 nm, more preferably 1 to 5,000 nm, more preferably 1 to 1,000 nm, more preferably 1 to 500 nm. The cathode metal, such as a Mg/Ag alloy or a binary Li—Al system of ca. 200 nm is laminated on the top of the organic layers. The vacuum during the deposition is preferably less than 0.1333 Pa ($1 \times 10^{-3}$ Torr), more preferably less than $1.333 \times 10^{-3}$ Pa ($1 \times 10^{-5}$ Torr), more preferably less than $1.333 \times 10^{-4}$ Pa ($1 \times 10^{-5}$ Torr).

As anode usual anode materials which possess high work function such as metals like gold, silver, copper, aluminum, indium, iron, zinc, tin, chromium, titanium, vanadium, cobalt, nickel, lead, manganese, tungsten and the like, metallic alloys such as magnesium/copper, magnesium/silver, magnesium/aluminum, aluminum/indium and the like, semiconductors such as Si, Ge, GaAs and the like, metallic oxides such as indium-tin-oxide ("ITO"), ZnO and the like, metallic compounds such as CuI and the like, and furthermore, electroconducting polymers such as polyacetylene, polyaniline, polythiophene, polypyrrole, polyparaphenylene and the like, preferably ITO, most preferably ITO on glass as substrate can be used. Of these electrode materials, metals, metallic alloys, metallic oxides and metallic compounds can be transformed into electrodes, for example, by means of the sputtering method. In the case of using a metal or a metallic alloy as a material for an electrode, the electrode can be formed also by the vacuum deposition method. In the case of using a metal or a metallic alloy as a material forming an electrode, the electrode can be formed by the chemical plating method (see for example, Handbook of Electrochemistry, pages 383-387, Mazuren, 1985). In the case of using an electroconducting polymer, an electrode can be made by forming it into a film by means of an anodic oxidation polymerization method onto a substrate which has been previously provided with an electroconducting coating. The thickness of an electrode to be formed on a substrate is not limited to a particular value, but, when the substrate is used as a light emitting plane, the thickness of the electrode is preferably within the range of from 1 nm to 100 nm, more preferably, within the range of from 5 to 50 nm, so as to ensure transparency.

In a preferred embodiment ITO is used on a substrate having an ITO film thickness in the range of from 10 nm (100 Å) to 1μ (10000 Å), preferably from 20 nm (200 Å) to 500 nm (5000 Å). Generally, the sheet resistance of the ITO film is chosen in the range of not more than 100 $\Omega/cm^2$, preferably not more than 50 $\Omega cm^2$.

Such anodes are commercially available from Japanese manufacturers, such as Geomatech Co. Ltd., Sanyo Vacuum Co. Ltd., Nippon Sheet Glass Co. Ltd.

As substrate either an electronconducting or electrically insulating material can be used. In case of using an electroconducting substrate, a light emitting layer or a positive hole transporting layer is directly formed thereupon, while in case of using an electrically insulating substrate, an electrode is firstly formed thereupon and then a light emitting layer or a positive hole transporting layer is superposed.

The substrate may be either transparent, semi-transparent or opaque. However, in case of using a substrate as an indicating plane, the substrate must be transparent or semi-transparent.

Transparent electrically insulating substrates are, for example, inorganic compounds such as glass, quartz and the like, organic polymeric compounds such as polyethylene, polypropylene, polymethylmethacrylate, polyacrylonitrile, polyester, polycarbonate, polyvinylchloride, polyvinylalcohol, polyvinylacetate and the like. Each of these substrates can be transformed into a transparent electroconducting substrate by providing it with an electrode according to one of the methods described above.

Examples of semi-transparent electrically insulating substrates are inorganic compounds such as alumina, YSZ (yttrium stabilized zirconia) and the like, organic polymeric compounds such as polyethylene, polypropylene, polystyrene, epoxy resins and the like. Each of these substrates can be transformed into a semi-transparent electroconducting substrate by providing it with an electrode according to one of the above-mentioned methods.

Examples of opaque electroconducting substrates are metals such as aluminum, indium, iron, nickel, zinc, tin, chromium, titanium, copper, silver, gold, platinum and the like, various elctroplated metals, metallic alloys such as bronze, stainless steel and the like, semiconductors such as Si, Ge, GaAs, and the like, electroconducting polymers such as polyaniline, polythiophene, polypyrrole, polyacetylene, polyparaphenylene and the like.

A substrate can be obtained by forming one of the above listed substrate materials to a desired dimension. It is preferred that the substrate has a smooth surface. Even if it has a rough surface, it will not cause any problem for practical use, provided that it has round unevenness having a curvature of not less than 20 μm. As for the thickness of the substrate, there is no restriction as far as it ensures sufficient mechanical strength.

As cathode usual cathode materials which possess low work function such as alkali metals, earth alkaline metals, group 13 elements, silver, and copper as well as alloys or mixtures thereof such as sodium, lithium, potassium, sodium-potassium alloy, magnesium, magnesium-silver alloy, magnesium-copper alloy, magnesium-aluminum alloy, magnesium-indium alloy, aluminum, aluminum-aluminum oxide alloy, aluminum-lithium alloy, indium, calcium, and materials exemplified in EP-A 499,011 such as electroconducting polymers e.g. polypyrrole, polythiophene, polyaniline, polyacetylene etc., preferably Mg/Ag alloys, or Li—Al compositions can be used.

In a preferred embodiment a magnesium-silver alloy or a mixture of magnesium and silver, or a lithium-aluminum alloy or a mixture of lithium and aluminum can be used in a film thickness in the range of from 10 nm (100 Å) to 1 μm (10000 Å), preferably from 20 nm (200 Å) to 500 nm (5000 Å).

Such cathodes can be deposited on the foregoing electron transporting layer by known vacuum deposition techniques described above.

In a preferred embodiment of this invention a light-emitting layer can be used between the hole transporting layer and the electron transporting layer. Usually the light-emitting layer is prepared by forming a thin film on the hole transporting layer.

As methods for forming said thin film, there are, for example, the vacuum deposition method, the spin-coating method, the casting method, the Langmuir-Blodgett ("LB") method and the like. Among these methods, the vacuum deposition method, the spin-coating method and the casting method are particularly preferred in view of ease of operation and cost.

In case of forming a thin film using a composition by means of the vacuum deposition method, the conditions under which the vacuum deposition is carried out are usually strongly dependent on the properties, shape and crystalline state of the compound(s). However, optimum conditions are usually as follows: temperature of the heating boat: 100 to 400° C.; substrate temperature: −100 to 350° C.; pressure: $1.33 \times 10^4$ Pa ($1 \times 10^2$ Torr) to $1.33 \times 10^{-4}$ Pa ($1 \times 10^{-6}$ Torr) and deposition rate: 1 pm to 6 nm/sec.

In an organic EL element, the thickness of the light emitting layer is one of the factors determining its light emission properties. For example, if a light emitting layer is not sufficiently thick, a short circuit can occur between the two electrodes sandwiching said light emitting layer, and therefor, no EL emission is obtained. On the other hand, if the light emitting layer is excessively thick, a large potential drop occurs inside the light emitting layer because of its high electrical resistance, so that the threshold voltage for EL emission increases. Accordingly, the thickness of the organic light emitting layer is limited to the range of from 5 nm to 5 μm, preferably to the range of from 10 nm to 500 nm.

In the case of forming a light emitting layer by using the spin-coating method and the casting method, the coating can be carried out using a solution prepared by dissolving the composition in a concentration of from 0.0001 to 90% by weight in an appropriate organic solvent such as benzene, toluene, xylene, tetrahydrofurane, methyltetrahydrofurane, N,N-dimethylformamide, dichloromethane, dimethylsulfoxide and the like. If the concentration exceeds 90% by weight, the solution usually is so viscous that it no longer permits forming a smooth and homogenous film. On the other hand, if the concentration is less than 0.0001% by weight, the efficiency of forming a film is too low to be economical. Accordingly, a preferred concentration of the composition is within the range of from 0.01 to 80% by weight.

In the case of using the above spin-coating or casting method, it is possible to further improve the homogeneity and mechanical strength of the resulting layer by adding a polymer binder to the solution for forming the light emitting layer. In principle, any polymer binder may be used, provided that it is soluble in the solvent in which the composition is dissolved. Examples of such polymer binders are polycarbonate, polyvinylalcohol, polymethacrylate, polymethylmethacrylate, polyester, polyvinylacetate, epoxy resin and the like. However, if the solid content composed of the polymer binder and the composition exceeds 99% by weight, the fluidity of the solution is usually so low that it is impossible to form a light emitting layer excellent in homogeneity. On the other hand, if the content of the composition is substantially smaller than that of the polymer binder, the electrical resistance of said layer is very large, so that it does not emit light unless a high voltage is applied thereto. Accordingly, the preferred ratio of the polymer binder to the composition is chosen within the range of from 10:1 to 1:50 by weight, and the solid content composed of both components in the solution is preferably within the range of from 0.01 to 80% by weight, and more preferably, within the range of 0.1 to 60% by weight.

As hole-transporting layers known organic hole transporting compounds such as polyvinyl carbazole

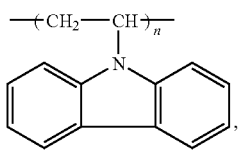

a TPD compound disclosed in J. Amer. Chem. Soc. 90 (1968) 3925:

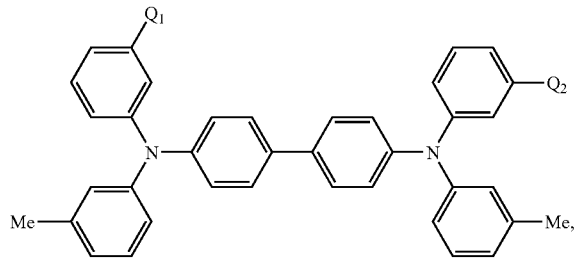

wherein $Q_1$ and $Q_2$ each represent a hydrogen atom or a methyl group;
a compound disclosed in J. Appl. Phys. 65(9) (1989) 3610:

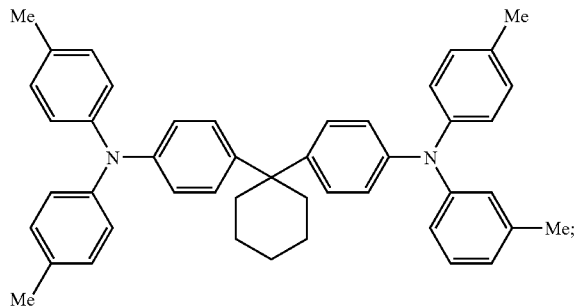

a stilbene based compound

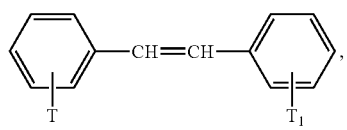

wherein T and $T_1$ stand for an organic radical;
a hydrazone based compound

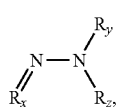

wherein Rx, Ry and Rz stand for an organic radical, and the like can be used.

Compounds to be used as a positive hole transporting material are not restricted to the above listed compounds. Any compound having a property of transporting positive holes can be used as a positive hole transporting material such as triazole derivatives, oxadiazole derivatives, imidazole derivatives, polyarylalkane derivatives, pyrazoline derivative, pyrazolone derivatives, phenylene diamine derivatives, arylamine derivatives, amino substituted chalcone derivatives, oxazole derivatives, stilbenylanthracene derivatives, fluorenone derivatives, hydrazone derivatives, stilbene derivatives, copolymers of aniline derivatives, electro-conductive oligomers, particularly thiophene oligomers, porphyrin compounds, aromatic tertiary amine compounds, stilbenyl amine compounds etc. Particularly, aromatic tertiary amine compounds such as N,N,N',N'-tetraphenyl-4,4'-diaminobiphenyl, N,N'-diphenyl-N,N'-bis(3-methylphenyl)-4,4'-diaminobiphenyl (TPD), 2,2'-bis(di-p-torylaminophenyl)propane, 1,1'-bis(4-di-toriaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quaterphenyl, N,N,N-tri(p-tolyl)amine, 4-(di-p-tolylamino)-4'-[4-(di-p-tolylamino)stilyl]stilbene, 4-N,N-diphenylamino-(2-diphenylvinyl)benzene, 3-methoxy-4'-N,N-diphenylaminostilbene, N-phenylcarbazole etc. are used.

Furthermore, 4,4'-bis[N-(1-naphtyl)-N-phenylamino]biphenyl disclosed in U.S. Pat. No. 5,061,569 and the compounds disclosed in EP-A-508,562, in which three triphenylamine units are bound to a nitrogen atom, such as 4,4',4"-tris[N-(3-methylphenyl)-N-phenylamino]triphenylamine, can be used.

A positive hole transporting layer can be formed by preparing an organic film containing at least one positive hole transporting material on the anode. The positive hole transporting layer can be formed by the vacuum deposition method, the spin-coating method, the casting method, the LB method and the like. Of these methods, the vacuum deposition method, the spin-coating method and the casting method are particularly preferred in view of ease and cost.

In the case of using the vacuum deposition method, the conditions for deposition may be chosen in the same manner as described for the formation of the light emitting layer (see above). If it is desired to form a positive hole transporting layer comprising more than one positive hole transporting material, the coevaporation method can be employed using the desired compounds.

In the case of forming a positive hole transporting layer by the spin-coating method or the casting method, the layer can be formed under the conditions described for the formation of the light emitting layer (see above).

As in the case of forming the light emitting layer a smoother and more homogeneous positive hole transporting layer can be formed by using a solution containing a binder and at least one positive hole transporting material. The coating using such a solution can be performed in the same manner as described for the light emitting layer. Any polymer binder may be used, provided that it is soluble in the solvent in which the at least one positive hole transporting material is dissolved. Examples of appropriate polymer binders and of appropriate and preferred concentrations are given above when describing the formation of the light emitting layer.

The thickness of the positive hole transporting layer is preferably chosen in the range of from 0.5 to 1000 nm, preferably from 1 to 100 nm, more preferably from 2 to 50 nm.

As hole injection materials known organic hole transporting compounds such as metal-free phthalocyanine ($H_2Pc$), copper-phthalocyanine (Cu—Pc) and their derivatives as described, for example, in JP64-7635 can be used. Furthermore, some of the aromatic amines defined as hole transporting materials above, which have a lower ionisation potential than the hole transporting layer, can be used.

An hole injection layer can be formed by preparing an organic film containing at least one hole injection material between the anode layer and the hole transporting layer. The hole injection layer can be formed by the vacuum deposition method, the spin-coating method, the casting method, the LB method and the like. The thickness of the layer is preferably from 5 nm to 5 μm, and more preferably from 10 nm to 100 nm.

The electron transporting materials should have a high electron injection efficiency (from the cathode) and a high electron mobility. The following materials can be exemplified for electron transporting materials: tris(8-hydroxyquinolinato)-aluminum(III) and its derivatives, bis(10-hydroxybenzo[h]quinolinolato)beryllium(II) and its derivatives, oxadiazole derivatives, such as 2-(4-biphenyl)-5-(4-tert.-butylphenyl)-1,3,4-oxadiazole and its dimer systems, such as 1,3-bis(4-tert.-butylphenyl-1,3,4)oxadiazolyl)biphenylene and 1,3-bis(4-tert.-butylphenyl-1,3,4-oxadiazolyl)phenylene, dioxazole derivatives, triazole derivatives, coumarine derivatives, imidazopyridine derivatives, phenanthroline derivatives or perylene tetracarboxylic acid derivatives disclosed in Appl. Phys. Lett. 48 (2) (1986) 183.

An electron transporting layer can be formed by preparing an organic film containing at least one electron transporting material on the hole transporting layer or on the light-emitting layer. The electron transporting layer can be formed by the vacuum deposition method, the spin-coating method, the casting method, the LB method and the like.

It is preferred that the positive hole inhibiting materials for a positive hole inhibiting layer have high electron injection/transporting efficiency from the electron transporting layer to the light emission layer and also have higher ionisation potential than the light emitting layer to prevent the flowing out of positive holes from the light emitting layer to avoid a drop in luminescence efficiency. As the positive hole inhibiting material known materials, such as Balq, TAZ and phenanthroline derivatives, e.g. bathocuproine (BCP), can be used:

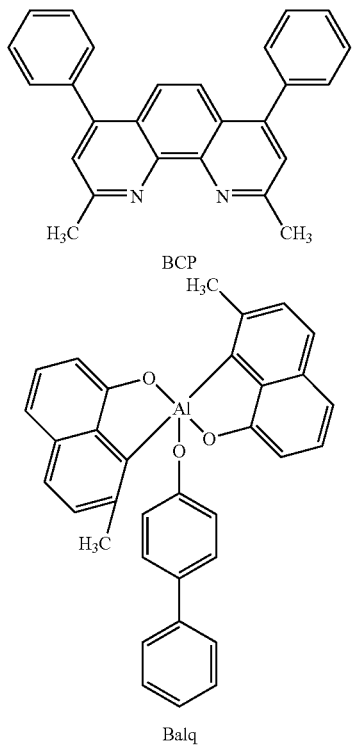

BCP

Balq

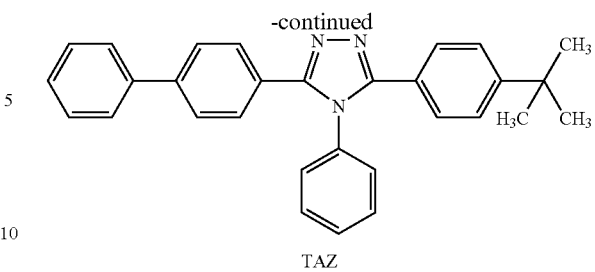

TAZ

The positive hole inhibiting layer can be formed by preparing an organic film containing at least one positive hole inhibiting material between the electron transporting layer and the light-emitting layer. The positive hole inhibiting layer can be formed by the vacuum deposition method, the spin-coating method, the casting method, the LB method and the like. The thickness of the layer preferably is chosen within the range of from 5 nm to 2 μm, and more preferably, within the range of from 10 nm to 100 nm.

As in the case of forming a light emitting layer or a positive hole transporting layer, a smoother and more homogeneous electron transporting layer can be formed by using a solution containing a binder and at least one electron transporting material.

The thickness of an electron transporting layer is chosen in the range of from 0.5 to 1000 nm, preferably from 1 to 100 nm, more preferably from 2 to 50 nm.

The light-emitting compositions have a fluorescence emission maximum in the range of from 500 to 780, preferably from 520 to 750, more preferred from 540 to 700 nm. Further, the inventive compounds preferably exhibit an absorption maximum in the range of 450 to 580 nm.

The light-emitting compositions usually exhibit a fluorescence quantum yield ("FQY") in the range of from 1>FQY≧0.3 (measured in aerated toluene or DMF). Further, in general, the inventive compositions exhibit a molar absorption coefficient in the range of from 5000 to 100000.

It is possible that the light-emitting layer can consist of two or more fluorescent substances of formula I for energy donor(s) and/or energy acceptor(s).

Another embodiment of the present invention relates to a method of coloring high molecular weight organic materials (having a molecular weight usually in the range of from $10^3$ to $10^7$ g/mol; comprising biopolymers, and plastic materials, including fibres) by incorporating therein the inventive fluorescent DPP compounds of formula I by known methods in the art.

The inventive DPP compounds of the formula I can be used, as described for the DPP compounds of formula I' in EP-A-1087005, for the preparation of inks, for printing inks in printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fiber tips, card, wood, (wood) stains, metal, inking pads or inks for impact printing processes (with impact-pressure ink ribbons), for the preparation of colorants, for coating materials, for industrial or commercial use, for textile decoration and industrial marking, for roller coatings or powder coatings or for automotive finishes, for high-solids (low-solvent), water-containing or metallic coating materials or for pigmented formulations for aqueous paints, for the preparation of pigmented plastics for coatings, fibers, platters or mold carriers, for the preparation of non-impact-printing material for digital printing, for the thermal wax transfer printing process, the ink jet printing process or for the thermal transfer printing process, and also for the preparation of color filters, especially for visible light in the range from 400 to 700 nm, for liquid-crystal displays (LCDs) or charge combined devices (CCDs) or for the preparation of cosmetics or for the preparation of polymeric ink particles, toners, dye lasers, dry copy toners liquid copy toners, or electrophotographic toners, and electroluminescent devices.

Illustrative examples of suitable organic materials of high molecular weight which can be colored with the inventive fluorescent DPP compounds of formula I are described in EP-A-1,087,005.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic materials may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the inventive fluorescent DPP compounds of formula I are used for the mass coloration of polyvinyl chloride, polyamides, polymethylmethacrylates and, especially, polyolefins such as polyethylene and polypropylene as well as for the preparation of paint systems, including powder coatings, inks, printing inks, color filters and coating colors.

Illustrative examples of preferred binders for paint systems are alkyd/melamine resin paints, aryl/melamine resin paints, cellulose acetate/cellulose butyrate paints and two-pack system lacquers based on acrylic resins which are crosslinkable with polyisocyanate.

According to observations made to date, the inventive fluorescent DDP compounds of formula I can be added in any desired amount to the material to be colored, depending on the end use requirements.

Hence, another embodiment of the present invention relates to a composition comprising (a) 0.01 to 50, preferably 0.01 to 5, particularly preferred 0.01 to 2% by weight, based on the total weight of the colored high molecular organic material, of a fluorescent DPP compound of formula I according to the present invention, and (b) 99.99 to 50, preferably 99.99 to 95, particularly preferred 99.99 to 98% by weight, based on the total weight of the colored high molecular organic material, of a high molecular organic material, and (c) optionally, customary additives such as rheology improvers, dispersants, fillers, paint auxiliaries, siccatives, plasticizers, UV-stabilizers, and/or additional pigments or corresponding precursors in effective amounts, such as e.g. from 0 to 50% by weight, based on the total weight of (a) and (b).

To obtain different shades, the inventive fluorescent DPP compounds of formula I may advantageously be used in admixture with fillers, transparent and opaque white, colored and/or black pigments as well as customary luster pigments in the desired amount.

For the preparation of paint systems, coating materials, color filters, inks and printing inks, the corresponding high molecular weight organic materials, such as binders, synthetic resin dispersions etc. and the inventive fluorescent DDP compounds of formula I are usually dispersed or dissolved together, if desired together with customary additives such as dispersants, fillers, paint auxiliaries, siccatives, plasticizers and/or additional pigments or pigment precursors, in a common solvent or mixture of solvents.

Hence, a further embodiment of the present invention relates to a method of using the inventive fluorescent DDP compounds of formula I for the preparation of dispersions and the corresponding dispersions, and paint systems, coating materials, color filters, inks and printing inks comprising the inventive fluorescent DDP compounds of formula I.

A particularly preferred embodiment relates to the use of the inventive DDP compounds of formula I for the preparation of fluorescent tracers for e.g. leak detection of fluids such as lubricants, cooling systems etc., as well as to fluorescent tracers or lubricants comprising the inventive DPP compounds of formula I.

A particular embodiment of this invention concerns ink jet inks comprising the inventive fluorescent compositions.

The desired ink may contain up to 30% by weight of the fluorescent composition, but will generally be in the range of 0.1 to 10, preferably from 0.1 to 8% by weight of the total ink composition for most thermal ink jet printing applications.

For the pigmentation of high molecular weight organic material, the inventive DPP compounds of formula I optionally in the form of masterbatches, usually, are mixed with the high molecular weight organic materials using roll mills, mixing apparatus or grinding apparatus. Generally, the pigmented material is subsequently brought into the desired final form by conventional processes, such as calandering, compression molding, extrusion, spreading, casting or injection molding.

For pigmenting lacquers, coating materials and printing inks the high molecular weight organic materials and the inventive DPP compounds of formula I, alone or together with additives, such as fillers, other pigments, siccatives or plasticizers, are generally dissolved or dispersed in a common organic solvent or solvent mixture. In this case it is possible to adopt a procedure whereby the individual components are dispersed or dissolved individually or else two or more are dispersed or dissolved together and only then are all of the components combined.

The present invention additionally relates to inks comprising a coloristically effective amount of the pigment dispersion of the inventive DDP compounds of formula I.

The weight ratio of the pigment dispersion to the ink in general is chosen in the range of from 0.001 to 75% by weight, preferably from 0.01 to 50% by weight, based on the overall weight of the ink.

The preparation and use of color filters or color-pigmented high molecular weight organic materials are well-known in the art and described e.g. in Displays 14/2, 1151 (1993), EP-A 784085, or GB-A 2,310,072.

The color filters can be coated for example using inks, especially printing inks, which can comprise pigment dispersions comprising the inventive DDP compounds of formula I or can be prepared for example by mixing a pigment dispersion comprising a DPP compound of formula I with chemically, thermally or photolytically structurable high molecular weight organic material (so-called resist). The subsequent preparation can be carried out, for example, in analogy to EP-A-654 711 by application to a substrate, such as a LCD (liquid crystal display), subsequent photostructuring and development.

Particular preference for the production of color filters is given to pigment dispersions comprising a DPP compound of formula I which possess non-aqueous solvents or dispersion media for polymers.

The present invention relates, moreover, to toners comprising a pigment dispersion containing a DPP compound of formula I or a high molecular weight organic material pigmented with a DPP compound of formula I in a colorstically effective amount.

The present invention additionally relates to colorants, colored plastics, polymeric ink particles, or non-impact-printing material comprising an inventive DPP pigment of formula I, preferably in the form of a dispersion, or a high molecular weight organic material pigmented with a DPP compound of formula I in a coloristically effective amount.

A coloristically effective amount of the pigment dispersion according to this invention comprising an inventive DPP compound of formula I denotes in general from 0.0001 to 99.99% by weight, preferably from 0.001 to 50% by weight and, with particular preference, from 0.01 to 50% by weight, based on the overall weight of the material pigmented therewith.

The DDP compounds of formula I can be applied to color polyamides, because they do not decompose during the incorporation into the polyamides. Further, they exhibit an exceptionally good lightfastness, a superior heat stability, especially in plastics.

The following examples illustrate various embodiments of the present invention, but the scope of the invention is not limited thereto.

EXAMPLES

Example 1

24.6 g (0.22 mol) of potassium t-butoxide, 41 g (0.20 mol) of 9-cyanophenanthrene and 200 ml of t-amyl alcohol were heated up to 100° C. under a nitrogen atmosphere. As soon as this temperature had been reached, a solution of 23 g (0.10 mol) of di-n-butyl succinate and 70 ml of t-amyl alcohol was added over 1 hour using a dropping funnel. When the addition is completed, the reaction mixture was kept for 16 hours at 100° C., cooled to 65° C., neutralised with 20 ml of glacial acetic acid and boiled briefly at reflux temperature. The resultant pigment suspension was filtered at room temperature. The filter cake was suspended in 300 ml of methanol and the pigment was isolated by filtration, then finally washed with methanol and water until washings run colourless, and dried at 100° C. in vacuum, affording 8.5 g of 1,4-diketo-3,6-bis-(9-phenanthrenyl)-pyrrolo-(3,4-c)-pyrrole.

2.2 g (4.5 mmol) of 1,4-diketo-3,6-bis-(9-phenanthrenyl)-pyrrolo-(3,4-c)-pyrrole was slurred in 30 ml of 1-methyl-2-pyrrolidinone for 2 hours at room temperature. 1.3 g (11.6 mmol) of potassium t-butoxide are added to the slurry under nitrogen. After stirring for 2 hours, 2.07 g (11.2 mmol) of 3,5-dimethylbenzyl bromide were added to the reaction mixture and then the mixture is additionally stirred for 2 hours. The mixture was poured into 50 ml of water and the yellow solid was filtered off and purified by column chromatography (silica gel, dichloromethane as eluent). After drying 1.89 g (58%) of a red solid were obtained.

Example 2

Example 1 was repeated except that 3,5-di-t-butylbenzyl bromide was used as alkylating agent, whereby a red solid (yield: 36%) was obtained.

Example 3

Example 1 was repeated except that methyl iodide was used as alkylating agent, whereby an orange solid (yield: 48%) was obtained.

Example 4

Example 1 was repeated except that n-butyl iodide was used as alkylating agent, whereby an orange solid (yield: 25%) was obtained.

Example 5

15.7 g (0.14 mol) of potassium t-butoxide, 28 g (0.12 mol) of 4-bromonaphtalene-1-carbonitrile and 200 ml of t-amyl alcohol were heated up to 100° C. under a nitrogen atmosphere. As soon as the this temperature had been reached, a solution of 13.8 g (0.06 mol) of di-n-butyl succinate and 70 ml of t-amyl alcohol was added over 1 hour using a dropping funnel. When the addition had been completed, the reaction mixture was kept for 16 hours at 100° C., then cooled to 50° C. neutralised with 15 ml of glacial acetic acid and boiled briefly at reflux temperature. The resultant pigment suspension was filtered at room temperature. The filter cake was suspended in 300 ml of methanol and the pigment was isolated by filtration, finally washed with methanol and water until washings ran colourless, and dried at 100° C. in vacuum. Affording 3.9 g (12%) of 1,4-diketo-3,6-bis-(4-bromonaphtyl)-pyrrolo-(3,4-c)-pyrrole.

2.2 g (4.0 mmol) of 1,4-diketo-3,6-bis-(4-bromonaphtyl)-pyrrolo-(3,4-c)-pyrrole were slurred in 30 ml of 1-methyl-2-pyrrrolidinone for 2 hours at room temperature. 1.15 g (10.3 mmol) of potassium t-butoxide were added to the slurry under nitrogen. After stirring for 2 hours, 1.79 g (9.7 mmol) of 3-methylbenzyl bromide were added to the reaction mixture and then the mixture was additionally stirred for 2 hours. The mixture was poured into 50 ml of water and the yellow solid was filtered off and purified by column chromatography (silica gel, dichloromethane as eluent). After drying 0.98 g (34%) of 2,5-bis-(3-methylbenzyl)-1,4-diketo-3,6-bis-(4-bromonaphtyl)-pyrrolo-3,4-c)-pyrrole were obtained.

0.73 g (1.0 mmol) of 2,5-bis-(3-methylbenzyl)-1,4-diketo-3,6-bis-(4-bromonaphtyl)-pyrrolo-(3,4c)-pyrrole, 4.25 g (2.5mmol) of diphenylamine, 5 mg of Palladium(II)acetate, 1 mg of tri-t-butylphosphine and 50 ml of dry xylene were place in a 100 ml three-necked flask and stirred at 120° C. under a nitrogen atmosphere for 15 hours. After the reaction had been completed, xylene was removed under reduced pressure and the residue was purified by column chromatography (silica gel, dichloromethane as eluent). After drying 0.6 g of the following product was obtained as red solid.

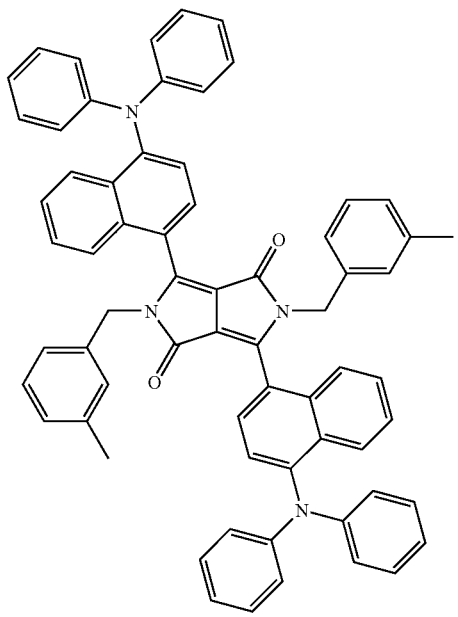

Example 6

Example 5 was repeated except that 4,4'-dimethoxydiphenylamine was used instead of diphenylamine. The following compound was obtained as red solid.

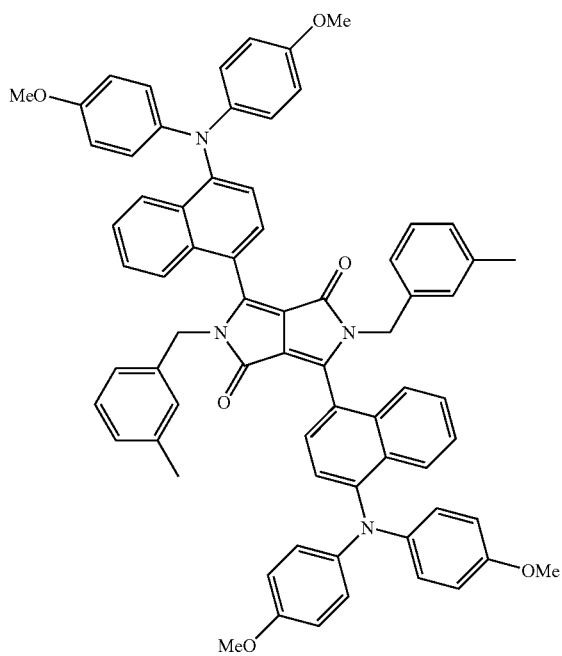

Example 7

Example 1 was repeated except that 4-methylbenzyl bromide was used as alkylating agent, whereby the following compound was obtained.

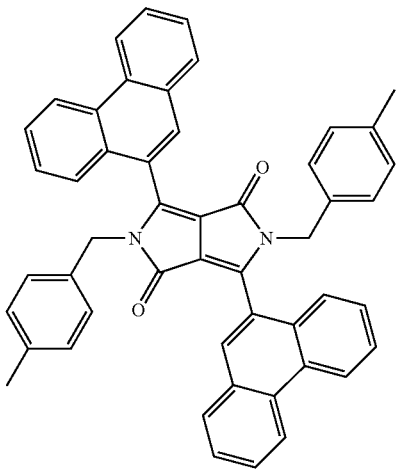

Example 8

A glass substrate (manufactured by Asahi Glass Co., a product prepared by electron beam vapor deposition method) on which an ITO transparent electroconductive film had been deposited up to a thickness of 150 nm was cut into a size of 30×40 mm, and etched. The substrate thus obtained was subjected to ultrasonic washing with acetone for 15 minutes and then with Semikoklin 56 for 15 minutes, and then washed with ultra-pure water. Subsequently, the substrate was subjected to ultrasonic washing with isopropyl alcohol for 15 minutes, dipped in hot methanol for 15 minutes, and then dried. Just before forming the substrate into an element, the substrate thus obtained was subjected to an UV-ozone treatment for one hour and placed in a vacuum vapor deposition apparatus, and the apparatus was evacuated until the inner pressure reached $1 \times 10^{-5}$ Pa or less. Then, according to the resistance heating method, N,N'-diphenyl-N,N'-(3-methylphenyl)-1,1'-diphenyl-4,4'-diamine (TPD) was vapor-deposited as a positive hole transporting material up to a thickness of 50 nm, to form a positive hole transporting layer. Subsequently, the DPP compound obtained in example 7 as a light emitting material was vapor-deposited up to a thickness of 50 nm to form a light emitting layer. Subsequently, a Mg—Ag alloy (10:1) was vapor-deposited to form a cathode having a thickness of 150 nm, and an element having a size of 5×5 mm square was prepared.

The luminescent peak wavelength of the luminescent element thus obtained was 563 nm, and the maximum luminance thereof was 16,940 Cd/m².

Example 9

Example 1 was repeated except that benzyl bromide was used as alkylating agent, whereby an orange solid (yield: 35%) was obtained.

Example 10

Example 8 was repeated except that the compound obtained in example 9 was used as a light emitting material. The maximum luminance thereof was 10170 Cd/m².

Example 11

Example 8 was repeated except that the compound obtained in example 1 was used as a light emitting material. The maximum luminance thereof was 7400 Cd/m².

Example 12

Example 8 was repeated except that the compound obtained in example 2 was used as a light emitting material. The maximum luminance thereof was 5710 Cd/m².

Example 13

Example 8 was repeated except that the compound obtained in example 3 was used as a light emitting material. The maximum luminance thereof was 6180 Cd/m².

Example 14

Example 8 is repeated except that the compound obtained in example 4 was used as a light emitting material. The maximum luminance thereof was 12170 Cd/m².

Example 15

Example 1 is repeated except that ethyl iodide is used as alkylating agent, whereby an orange solid (yield: 38%) is obtained.

Example 16

Example 1 was repeated except that ethyl iodide was used as alkylating agent, whereby the following compound was obtained.

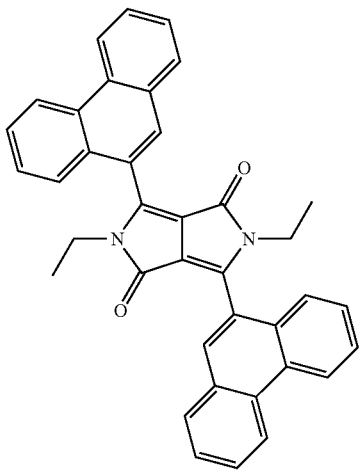

Example 17

Example 8 was repeated except that the compound obtained in example 16 was used as a light emitting material. The maximum luminance thereof was 13,940 Cd/m².

Comparative Example 1

Example 8 was repeated except that the comparative compound 1 shown below (example 81 of EP-A-1,087,006) was used as a light emitting material. The maximum luminance thereof was 5260 Cd/m².

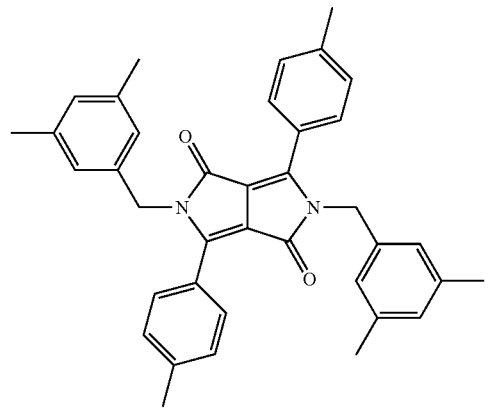

Comparative Compound 1

The present invention can provide a luminescent element high in the efficiency of electrical energy utilisation, high in luminance and high in colour purity.

The invention claimed is:

1. An electroluminescent device comprising a fluorescent diketopyrrolopyrrole of the formula

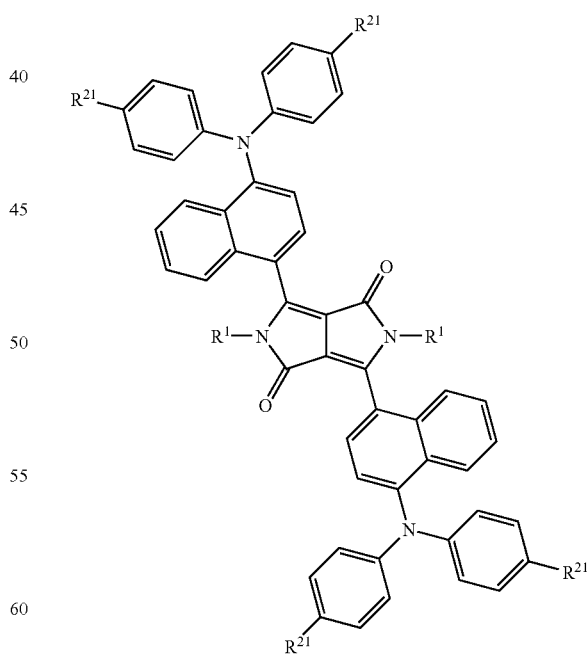

wherein $R^1$ is $C_1$-$C_8$alkyl or —$CH_2$-$A^3$, wherein $A^3$ stands for phenyl, which can be substituted one or two times with $C_1$-$C_8$alkyl, and $R^{21}$ is hydrogen, $C_1$-$C_4$alkyl or $C_1$-$C_4$alkoxy.

2. An electroluminescent device comprising a fluorescent diketopyrrolopyrrole of the formula
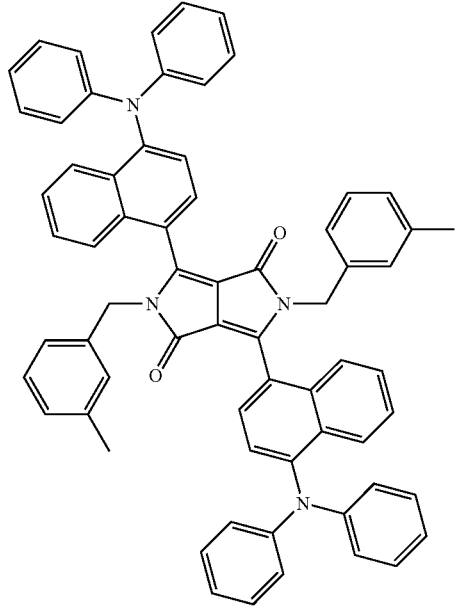
or
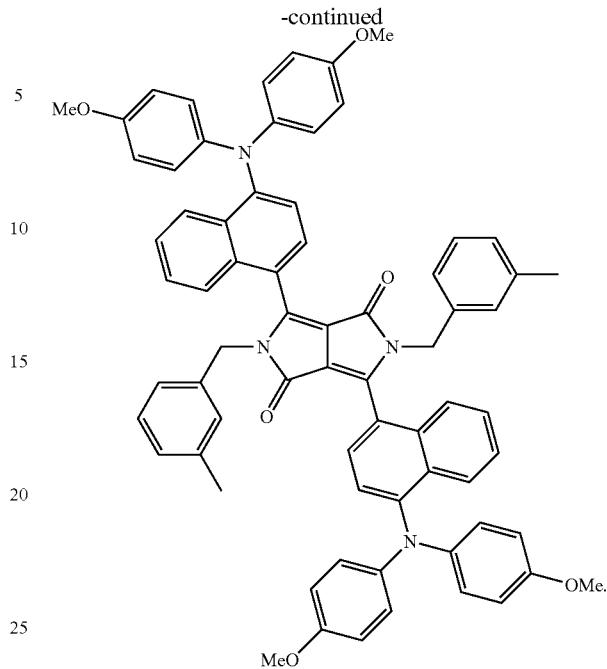
* * * * *